United States Patent [19]

Atwal

[11] Patent Number: 4,824,831
[45] Date of Patent: Apr. 25, 1989

[54] 4,5-DIHYDRO-1H-BENZAZEPINE-3-CARBOXYLIC ACID ESTERS WHICH ARE USEFUL AS ANTI-HYPERTENSIVE AGENTS

[75] Inventor: Karnail Atwal, Cranbury, N.J.

[73] Assignee: E. R. Squibb & Sons, Inc., Princeton, N.J.

[21] Appl. No.: 135,960

[22] Filed: Dec. 21, 1987

[51] Int. Cl.$^4$ .............................................. A61K 31/55
[52] U.S. Cl. ...................................... 514/213; 540/593
[58] Field of Search .......................... 540/593; 514/213

[56] References Cited

U.S. PATENT DOCUMENTS

| | | | |
|---|---|---|---|
| 3,458,498 | 7/1969 | Koo et al. ........................... | 540/593 |
| 4,436,749 | 3/1984 | Hatinguais ........................ | 540/593 |
| 4,647,561 | 3/1987 | Atwal ................................. | 514/221 |
| 4,650,797 | 3/1987 | Atwal ................................. | 514/221 |
| 4,654,335 | 3/1987 | Atwal ................................. | 514/211 |

Primary Examiner—Mary C. Lee
Assistant Examiner—Zinna Northington
Attorney, Agent, or Firm—Lawrence S. Levinson; Theodore R. Furman, Jr.

[57] ABSTRACT

Compound of the formula

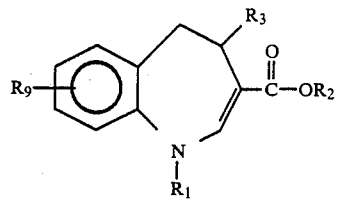

wherein $R_3$ is aryl and $R_1$ is hydrogen or

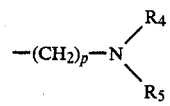

are disclosed. These compounds are useful as cardiovascular agents, and especially as anti-hypertensive agents.

11 Claims, No Drawings

4,5-DIHYDRO-1H-BENZAZEPINE-3-CARBOXYLIC ACID ESTERS WHICH ARE USEFUL AS ANTI-HYPERTENSIVE AGENTS

SUMMARY OF THE INVENTION

This invention relates to the novel 4,5-dihydro-1H-benzazepine-3-carboxylic acid esters of formula I and pharmaceutically acceptable salts thereof

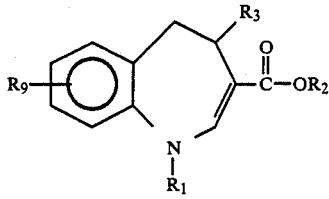

$R_1$ is hydrogen or

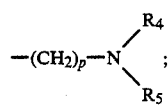

$R_2$ is hydrogen, lower alkyl, —$(CH_2)_m$—aryl, —$(CH_2)_m$—cycloalkyl, —$(CH_2)_p$—OH, —$(CH_2)_p$—O—lower alkyl, —$(CH_2)_p$—O—$(CH_2)_m$—aryl, —$(CH_2)_p$—SH, —$(CH_2)_p$—S—lower alkyl, —$(CH_2)_p$—S—$(CH_2)_m$—aryl,

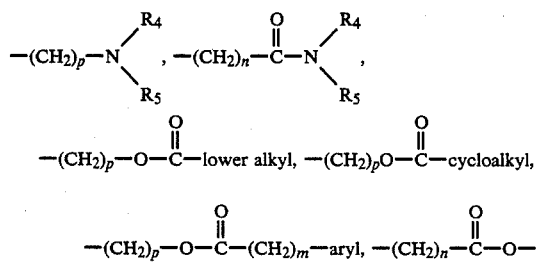

halo substituted lower alkyl, or a pharmaceutically acceptable salt forming ion;

$R_3$ is aryl;

$R_4$ and $R_5$ are independently selected from the group consisting of hydrogen, lower alkyl, —$(CH_2)_m$—aryl,

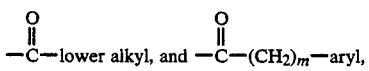

or $R_4$ and $R_5$ taken together with the N atom to which they are attached complete a heterocyclic ring of the formula

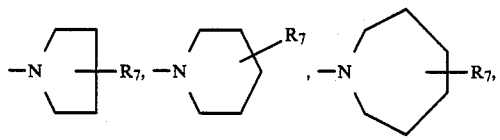

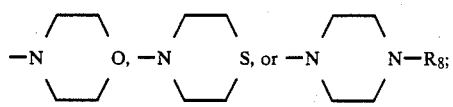

$R_6$ is hydrogen, lower alkyl, —$(CH_2)_m$—aryl, or a pharmaceutically acceptable salt forming ion;

$R_7$ is hydrogen, lower alkyl of 1 to 4 carbons, lower alkoxy of 1 to 4 carbons, lower alkylthio of 1 to 4 carbons, halo, $CF_3$ or hydroxy;

$R_8$ is hydrogen, lower alkyl of 1 to 4 carbons or $(CH_2)_m$—aryl;

$R_9$ is hydrogen, lower alkoxy of 1 to 4 carbons, halo or $CF_3$;

m is zero or an integer from 1 to 6;

n is an integer from 1 to 6;

p is an integer from 2 to 6.

DETAILED DESCRIPTION OF THE INVENTION

This invention in its broadest aspects relates to the 4,5-dihydro-1H-benzazepine-3-carboxylic acid esters of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl etc.

The term aryl refers to phenyl or mono substituted phenyl, wherein said substituent is lower alkyl of 1 to 4 carbons, lower alkylthio of 1 to 4 carbons, lower alkoxy of 1 to 4 carbons, halo, cyano, hydroxy, amino, —NH—alkyl wherein alkyl is of 1 to 4 carbons, —N(alkyl)$_2$ wherein alkyl is of 1 to 4 carbons, $CF_3$, $OCHF_2$,

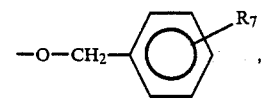

—O—$CH_2$—cycloalkyl,

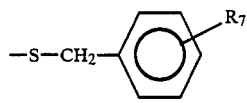

or —S—CH$_2$—cycloalkyl, di- or tri-substituted phenyl wherein said substituents are selected from methyl, methoxy, methylthio, halo, CF$_3$, hydroxy, amino, and OCHF$_2$.

The compounds of formula I can be prepared by first reacting a 2-nitrotoluene having the formula

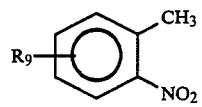

with a malonate having the formula

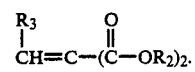

The reaction can be run in a polar nonprotic solvent (e.g. dimethylformamide), in the presence of a strong base such as sodium hydride, and yields a product having the formula

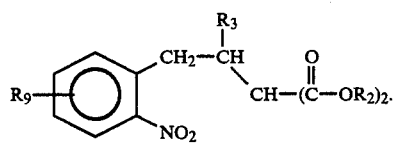

Reduction of a compound of formula IV yields the corresponding compound having the formula

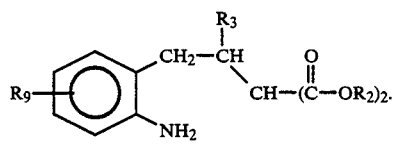

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) yields the corresponding benzazepine having the formula

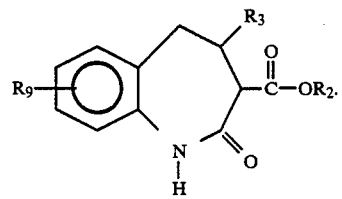

Treatment of compound VI in a solvent such as tetrahydrofuran, with a reducing agent, such as lithium aluminum hydride, provides a compound having the formula

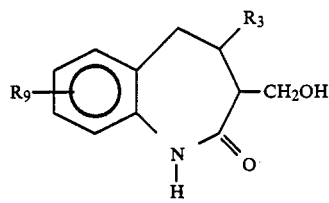

which can thereafter be treated with an acid, e.g. concentrated hydrochloric acid, in the presence of an alcoholic solvent, such as methanol, to yield

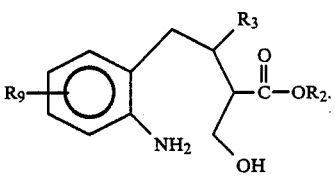

Compound VIII, in the presence of dimethylsulfoxide and triethylamine, can be treated with an oxidizing agent, e.g. pyridine-sulfur trioxide in dimethyl sulfoxide to provide

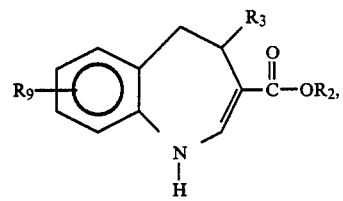

that is, the compounds of formula I wherein R$_1$ is hydrogen.

Treatment of the compound of formula IX in solvents, such as methylethylketone or dimethylformamide, with a base, such as potassium hydrogen carbonate or sodium hydride, followed by reaction with a compound having the formula

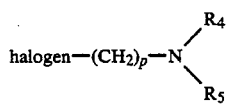

provides the compounds of formula I wherein R$_1$ is

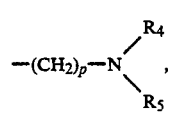

or salts thereof.

Preferred compounds of this invention are those wherein

R$_2$ is straight or branched chain lower alkyl of 1 to 5 carbons, —(CH$_2$)$_p$—O—lower alkyl wherein lower alkyl is straight or branched chain of 1 to 5 carbons,

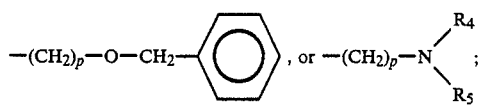

p is 2, 3 or 4;

R$_4$ and R$_5$ are independently selected from hydrogen, straight or branched chain lower alkyl of 1 to 5 carbons, and phenylethyl or substituted phenylethyl;

R$_3$ is phenyl, 2-, 3- or 4-mono substituted phenyl wherein said substituent is lower alkyl of 1 to 4 carbons lower alkoxy of 1 to 4 carbons, lower alkylthio of 1 to 4 carbons, halo, CF$_3$, or OCHF$_2$, disubstituted phenyl, 2,3,4-trisubstituted phenyl or 3,4,5-trisubstituted phenyl wherein said phenyl substituents are selected from methyl, methoxy, methylthio, halo, CF$_3$ and OCHF$_2$; and, R$_9$ is hydrogen, Cl or CF$_3$.

Most preferred are the above compounds wherein

R$_1$ is hydrogen or —(CH$_2$)$_2$—N(CH$_3$)$_2$;

R$_2$ is lower alkyl;

R$_3$ is phenyl, 2-(trifluoromethyl)phenyl, 4-methylphenyl, 4-methoxyphenyl or 2-chlorophenyl; and, R$_9$ is CF$_3$.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which R$_2$ is

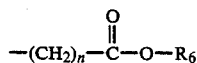

or in which R$_2$ is hydrogen include carboxylic acid salts, i.e. R$_2$ or R$_6$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg per kilogram of body weight per day, preferably from about 1 to about 50 mg per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-ischemic agents, as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will be further described by reference to the following examples however, the invention should not be limited to the details therein.

EXAMPLE 1

1-[2-(Dimethylamino)ethyl]-4,5-dihydro-4-(4-methoxyphenyl)-7-(trifluoromethyl)-1H-1-benzazepine-3-carboxylic acid, methyl ester, fumarate (1:1) salt

A.

[2-(5-Trifluoromethyl-2-nitrophenyl)-1-(4-methoxyphenyl)ethyl]propanedioic acid, dimethylester To a 2 liter three-neck flask (under nitrogen) was added 67 g (0.293 mol) of dimethyl-p-methoxybenzylidene malonate and 450 ml of dimethylformamide. The stirred solution was treated with a 50% sodium hydride dispersion (18.7 g, 0.39 mol). This mixture was treated dropwise with a solution of 2-methyl-4-trifluoromethylnitrobenzene (60.5 g, 0.293 mol) in 50 ml of dimethylformamide over a period of 1 hour while maintaining a temperature at about 28°-32° C. This mixture was stirred for 4 hours at room temperature, cooled, treated portionwise with 25 ml of acetic acid and poured onto a 2.5 l of ice water. The mixture was extracted 3 times with 250 ml of methylene chloride. The organic phases were combined, washed 3 times with 500 ml of water, dried over anhydrous magnesium sulfate, filtered and the solvent evaporated to give 126 g of a pale brown semi-solid. The latter was dissolved in 270 ml of methanol, cooled and filtered to give 72.8 g of a pale yellow product, m.p. 110°-112° C. A sample recrystallized from methanol, melted at 111°-113° C.

Analyst calc'd for C$_{21}$H$_{20}$NF$_3$O$_7$: C, 55.39; H, 4.43; N, 3.08; F, 12.52; Found: C, 56.08; H, 4.70; N, 2.96; F, 12.09.

[2-(5-Trifluoromethyl-2-aminophenyl)-1-(4-methoxyphenyl)ethyl]propanedioic acid, dimethylester A suspension of the title A compound (25 g, 0.055 mol) in 200 ml of methanol was treated with a cold suspension of 2.5 g of 5% palladium-on-carbon in 50 ml of methanol (under nitrogen) and placed on the Parr apparatus at 58 psi of hydrogen. After 30 minutes, the mixture was heated at 50°-55° for 1 hour, cooled to room temperature, removed from the Parr apparatus and allowed to stand at room temperature overnight. The flask was heated to dissolve the crystallized product and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, m.p. 124°–127° C. A sample of this material, after crystallization from methanol, melted at 125°–127° C.

Analysis calc'd for $C_{21}H_{22}NF_3O_5$: C, 59.29; H, 5.21; N, 3.29; F, 13.40; Found: C, 59.48; H, 5.26; N, 3.16; F, 13.43.

C.
7-(Trifluoromethyl)-1,3,4,5-tetrahydro-3-(methoxycarbonyl)-4-(4-methoxyphenyl)-2H-1-benzazepin-2-one A stirred solution of the title B compound (20 g, 0.047 mol) in 200 ml of methanol was treated with 13.3 ml of 25% sodium methoxide in methanol and heated to reflux (color lightened progressively from reddish to light yellow; also some solid separated during the heating). TLC (1:1 ethyl acetate/hexane) after 2.5 hours showed the reaction to be essentially complete. After a total of 2.75 hours of heating, the mixture was cooled in ice water and 70 ml of 1N hydrochloric acid was added to precipitate the partly gummy product. The latter became granular on rubbing and stirring in an ice water bath for 0.5 hours. The tan solid was filtered, washed with water and air dried to give 10.0 g of a pale yellow foam-like material. The latter was suspended in 30 ml of isopropyl alcohol, allowed to stand for 1 hour, filtered and washed with isopropyl alcohol and hexane to provide 13.64 g of the title C compound, m.p. 161°–163° C.

Analysis calc'd for $C_{20}H_{18}NF_3O_4$: C, 61.07; H, 4.61; N, 3.56; F, 14.49; Found: C, 61.26; H, 4.62; N, 3.41; F, 14.21.

D.
7-(Trifluoromethyl)-1,3,4,5-tetrahydro-3-hydroxymethyl-4-(4-methoxyphenyl)-2H-1-benzazepin-2-one To a suspension of lithium aluminum hydride (1.5 g, 0.04 mole) in dry tetrahydrofuran (50 ml) at −10° C. under argon was added slowly a solution of the title C compound (8 g, 0.02 mole) in dry tetrahydrofuran (50 ml) and stirred for 30 minutes. It was then quenched slowly with (1:1) mixture of tetrahydrofuran/water (50 ml) and diluted with diethyl ether, filtered through Celite. The layers were separated and organic layer was washed with water (50 ml), dried and concentrated in vacuo. It was triturated with isopropyl ether to yield 5.9 g of the title D compound as a white solid, m.p. 189°–190.5° C.

Analysis calc'd for $C_{19}H_{18}F_3NO_3$: C, 62.46; H, 4.97; N, 3.84; F, 15.59; Found: C, 62.35; H, 5.06; N, 3.84; F, 15.42.

E.
2-Amino-α-(hydroxymethyl)-β-(4-methoxyphenyl)-5-(trifluoromethyl)benzenebutanoic acid, methyl ester To a solution of the title D compound (2.5 g, 6.8 mmole) in 20 ml of dry methanol was added 5 ml of concentrated sulfuric acid slowly and then heated under reflux under argon for 5 hours. It was then diluted with water (100 ml) and methanol was evaporated off in vacuo, aqueous layer was extracted 3 times with ethyl acetate (200 ml), and washed with saturated sodium bicarbonate (50 ml), water (50 ml), dried and concentrated in vacuo to yield 1.7 g of the title E compound.

F.
4,5-Dihydro-4-(4-methoxyphenyl)-7-trifluoromethyl-1H-1-benzazepine-3-carboxylic acid, methyl ester To a solution of the title E compound (1.7 g, 4.2 mmole) in dry dimethyl sulfoxide (5 ml) was added triethyl amine (1.1 g, 10 mmole) and then a solution of pyridine-sulfur trioxide (2.4 g, 16.6 mmole) in dimethyl sulfoxide (5 ml) at room temperature and allowed to stir overnight. It was then diluted with diethyl ether and 10% hydrochloric acid. Aqueous layer was separated and extracted twice with diethyl ether (50 ml). Combined organic layer was washed twice with water (50 ml), dried over anhydrous magnesium sulfate and concentrated in vacuo. It was purified by flash chromatography eluting with (1:1) hexane/ethyl acetate mixture to yield 0.4 g of the title F compound as an oil.

G.
1-[2-(Dimethylamino)ethyl]-4,5-dihydro-4-(4-methoxyphenyl)-7-(trifluoromethyl)-1H-1-benzazepine-3-carboxylic acid, methyl ester, fumarate (1:1) salt To a suspension of sodium hydride (0.08 g, 1.6 mmole) in anhydrous dimethyl sulfoxide (5 ml) was added a solution of the title F compound (0.6 g, 1.6 mmole) in anhydrous dimethyl sulfoxide (2 ml) and stirred for 45 minutes at room temperature. A solution of dimethylaminoethyl chloride (1.1 ml of 2.2M solution in toluene, 2.4 mmole) was added and stirred for 1 hour and then heated at 65° for 2 hours. It was then poured into water (50 ml) and extracted 3 times with ethyl acetate (150 ml). Organic layer was then washed 3 times with water (50 ml), dried over anhydrous magnesium sulfate and concentrated in vacuo. It was purified by flash chromatography eluting with methylene chloride/methanol (9:1) mixture to give 0.6 g of the free amine. To a solution of this amine (0.6 g, 1.34 mmole) in methanol (5 ml) was added a solution of fumaric acid (0.16 g, 1.4 mmole) in hot methanol (2 ml) and stirred for 5 minutes. It was then concentrated in vacuo to a small amount of methanol and diluted with diethyl ether and filtered to give 0.42 g of the title compound, m.p. 198°–199° C.

Analysis calc'd for $C_{28}H_{31}F_3N_2O_7.0.24H_2O$: C, 59.11; H, 5.57; N, 4.92; Found: C, 59.11; H, 5.54; N, 4.89.

EXAMPLE 2
1-[2-Dimethylamino)ethyl]-4,5-dihydro-4-(4-methoxyphenyl)-6-(trifluoromethyl)-1H-benzazepine-3-carboxylic acid, methyl ester oxalate (1:1) salt

A.
[2-(6-Trifluoromethyl-2-nitrophenyl)-1-(4-methoxyphenyl)ethyl]propanedioic acid, dimethyl ester To a dry 3-neck flask (2 l) equipped with a stirrer, thermometer, condenser and dropping funnel was added dimethyl-p-methoxybenzylidene malonate (52.7 g, 0.21 ml) and dimethylformamide (350 ml). This solution was stirred (under nitrogen), treated with 60% sodium hydride (11 g, 0.27 mole) dispersion and this slurry was treated dropwise with a solution of 2-methyl-3-trifluoromethylnitrobenzene (43 g, 0.21 mol) in dimethylformamide (50 ml) over a period of 30 minutes while maintaining temperature at 28°–30°. The pale brown mixture was stirred at room temperature for 6 hours, allowed to stand overnight at room temperature, cooled and treated portionwise with acetic acid (20 ml). The pale yellow slurry was poured onto ice water (2 l) and extracted with methylene chloride (500 ml). The aqueous layer was extracted once with 250 ml of methylene chloride and then two more times with 100 ml of methylene chloride. The organic phases were combined, extracted three times with water (500 ml), dried over anhydrous magnesium sulfoxide, filtered and the solvent evaporated to give a pale brown granular solid (99.1 g). The latter was digested with hot methanol (150 ml). The suspension was allowed to cool to room temperature, cooled overnight, filtered, washed with cold methanol and dried to give 78.3 g of the title A compound as a colorless solid, m.p. 117°–119°.

Analysis calc'd for $C_{21}H_{20}NH_3O_7$: C, 55.39; H, 4.43; N, 3.08; F, 12.52; Found: C, 55,33; H, 4.38; N, 3.02; F, 12.43.

B.
[2-(6-Trifluoromethyl-2-aminophenyl)-1-(4-methoxyphenyl)ethyl]propanedioic acid, dimethyl ester The reduction of the title A compound was carried out as described for the title B compound in Example 1. The product was crystallized from methanol to yield the title B compound, m.p. 112°–114° C.

Analysis calc'd for $C_{21}H_{22}NF_3O_5$: C, 59.29; H, 5.21; N, 3.29; F, 13.40; Found: C, 59.04; H, 5.41; N, 3.27; F, 13.17.

C.
6-(Trifluoromethyl)-1,3,4,5-tetrahydro-3-(methoxycarbonyl)-4-(4-methoxyphenyl)-2H-1-benzazepin-2-one To a dry 3-neck flask (2 l) was added the title B compound (34.5 g, 0.081 mol) and methanol (350 ml). The suspension was heated to 45° and the resulting solution was cooled to 30° and treated with 25% solution of sodium methoxide in methanol (23 ml). This mixture was heated and refluxed for 1 hour. The slurry was cooled to 15° and treated with a solution of 6N hydrochloric acid in water (350 ml). After stirring in an ice bath for 2 hours, the pale gray solid was filtered and dried to give 30.8 g of the title C compound, m.p. 214°–216°.

Analysis calc'd for $C_{20}H_{18}NF_3O_4$: C, 61.07; H, 4.61; N, 3.56; F, 14.49; Found: C, 61.02; H, 4.56; N, 3.53; F, 14.30.

D.
6-(Trifluoromethyl)-1,3,4,5-tetrahydro-3-hydroxymethyl-4-(4-methoxyphenyl)-2H-1-benzazepin-2-one To a suspension of lithium aluminum hydride (2.9 g, 0.076 mole) in dry tetrahydrofuran (100 ml) at −10° C. under argon was added slowly a solution of the title C compound (15 g, 0.038 mole) in dry tetrahydrofuran (100 ml) and stirred for 30 minutes. It was then quenched slowly with (1:1) mixture of tetrahydrofuran/water (100 ml) and diluted with diethyl ether, filtered through Celite. The layers were separated and organic layer was washed with water (50 ml), dried and concentrated in vacuo. It was triturated with isopropyl ether to yield 11.8 g of the title D compound as a white solid, m.p. 189°–190.5° C.

Analysis calc'd for $C_{19}H_{18}F_3NO_3$: C, 62.46; H, 4.97; N, 3.84; F, 15.59; Found: C, 62.66; H, 5.11; N, 3.73; F, 15.77.

E.
2-Amino-α-(hydroxymethyl)-β-(4-methoxyphenyl)-6-(trifluoromethyl) benzenebutanoic acid, methyl ester To a solution of the title D compound (4 g, 10.9 mmole) in dry methanol (60 ml) was added concentrated sulfuric acid (12 ml) slowly and then heated under reflux under argon for 5 hours. It was then diluted with water (100 ml) and methanol was evaporated off in vacuo, aqueous layer was extracted with ethyl acetate (3×200 ml), and washed with saturated sodium bicarbonate (50 ml), water (50 ml), dried and concentrated in vacuo and purified by flash chromatography eluting with (1:1) hexane/ethyl acetate mixture to yield 3.2 g of the title E compound as an oil.

F.
4,5-Dihydro-4-(4-methoxyphenyl)-6-trifluoromethyl-1H-1-benzazepine-3-carboxylic acid, methyl ester To a solution of the title E compound (3.2 g, 7.8 mmole) in dry dimethyl sulfoxide (20 ml) was added triethyl amine (1.1 g, 10 mmole) and then a solution of pyridine-sulfur trioxide (2.4 g, 16.6 mmole) in dimethyl sulfoxide (10 ml) at room temperature and allowed to stir overnight. It was then diluted with diethyl ether and 10% hydrochloric acid. Aqueous layer was separated and extracted with diethyl ether (2×50 ml). Combined orgaic layers were washed with water (2×50 ml), dried over anhydrous magnesium sulfate and concentrated in vacuo. It was purified by flash chromatography eluting with (1:1) hexane/ethyl acetate mixture to yield 0.6 g of the title F compound as an oil.

G.
1-[2-(Dimethylamino)ethyl]-4,5-dihydro-4-(4-methoxyphenyl)-6-(trifluoromethyl)-1H-benzazepine-3-carboxylic acid, methyl ester oxalate (1:1) salt To a suspension of sodium hydride (0.166 g, 3.4 mmole) in anhydrous dimethyl sulfoxide (5 ml) was added a solution of the title F compound (1.3 g, 3.4 mmole) in anhydrous dimethyl sulfoxide (5 ml) and stirred for 45 minutes at room temperature. A solution of dimethylaminoethyl chloride (4 ml of 2.2M solution, 8.6 mmole) was added and stirred for 24 hours at room temperature. It was then poured into water (50 ml) and extracted 3 times with ethyl acetate (150 ml). Organic layer was then washed 3 times with water (50 ml), dried over anhydrous magnesium sulfate and concentrated in vacuo. It was purified by flash chromatography eluting with hexane/ethyl acetate (1:1), methylene chloride/methanol (95:5) to give 1 g of the free amine. To a solution of this amine (0.7 g, 1.56 mmole) in isopropanol (5 ml) was added a solution of oxalic acid (0.144 g, 1.56 mmole) in hot isopropanol (2 ml) and stirred for 5 minutes. It was then concentrated in vacuo and triturated with diethyl ether and filtered to give 0.6 g of the title compound, m.p. 115°–117° C.

Analysis calc'd for $C_{24}H_{27}F_3N_2O_3 \cdot C_2H_2O_4$: C, 57.99; H, 5.43; N, 5.20; F, 10.58; Found: C, 57.65; H, 5.31; N, 5.10; F, 10.66.

EXAMPLE 3

4-(2-Chlorophenyl)-4,5-dihydro-7-(trifluoromethyl)-1H-1-benzazepine-3-carboxylic acid, ethyl ester

A. [(2-Chlorophenyl)methylene]propanedioic acid, diethyl ester

A mixture of 97% chlorobenzaldehyde (51.5 g, 41.3 ml, 0.35 mole), diethyl malonate (57 g, 54 ml, 0.35 mole), acetic acid (1 ml) and piperdine (2 ml) in benzene (150 ml) was heated under reflux with azeotropic removal of water overnight. Benzene was removed by distillation, the residue was diluted with ethyl acetate (200 ml), washed with 10% hydrochloric acid, saturated potassium bicarbonate, brine and dried over anhydrous magnesium sulfate and concentrated in vacuo to yield 100 g of the title A compound as an oil.

B. [1-(2-Chlorophenyl)-2-[2-nitro-5-(trifluoromethyl)phenyl)ethyl]propanedioic acid, diethyl ester To a solution of the title A compound (80 g, 0.29 mole) in dimethylformamide (200 ml) was slowly added sodium hydride (13.8 g, 0.29 mole) at room temperature and stirred for 10 minutes. A solution of 2-methyl-4-trifluoromethylnitrobenzene (58.7 g, 0.29 mole) in dimethylformamide (20 ml) was added slowly under argon and allowed to stir at room temperature for 2 hours. It was then quenched with 30% acetic acid (10 ml) and extracted 3 times with ethyl acetate (150 ml). The organic layer was washed 3 times with water (100 ml), saturated sodium bicarbonate, brine, dried over anhydrous magnesium sulfate and concentrated in vacuo. It was purified by flash chromatography eluting with hexane (1 l), hexane/acetone (9:1) (2 l) to yield 72 g of the title B compound as an oil.

C. [2-[amino-5-(trifluoromethyl)phenyl]-1-(2-chlorophenyl)ethyl]propanedioic acid, diethyl ester To a solution of stannous chloride hydrate (57.9 g, 0.26 mole) in a mixture of methanol and concentrated hydrochloric acid (540/50 ml) was added a solution of the title B compound (25 g, 0.05 mole) in 20 ml of methanol and stirred mechanically under nitrogen for 16 hours. Celite (50 g) was added followed by the addition of ethyl acetate (200 ml) and solid potassium carbonate (50 g). The reaction was stirred for ~30 minutes, filtered through celite and concentrated in vacuo. It was diluted with ethyl acetate (300 ml) and washed twice with water (100 ml), dried over anhydrous magnesium sulfate and concentrated in vacuo to give 20 g of the crude product which was crystallized from isopropyl ether and hexane to give 15 g of the title C compound, m.p. 74°–76° C.

D. 4-(2-Chlorophenyl)-2,3,4,5-tetrahydro-2-oxo-7-(trifluoromethyl)-1H-1-benzazepine-3-carboxylic acid, methyl ester To a solution of the title C compound (5 g, 10.9 mmole) in 100 ml methanol was a solution of sodium methoxide 4.37M (6.3 ml, 27.4 mmole) in methanol and the reaction was heated at reflux for 4 hours under argon. It was then cooled down and quenched with a mixture of water/acetic acid/methanol (70/20/10) and then water (200 ml) was added and cooled in ice, precipitates were filtered off and dried to give 2.7 g of the title D compound, m.p. 183°–184° C.

E. [4-(2-Chlorophenyl)-1,3,4,5-tetrahydro-3-hydroxymethyl)-7-(trifluoromethyl)-2H-1-benzazepin-2-one To a suspension of lithium aluminum hydride (2.1 g, 0.058 mole) in dry tetrahydrofuran (100 ml) at −10° under argon was added a solution of the title D compound (11 g, 0.20 mole) in 20 ml of dry tetrahydrofuran slowly (~30 minutes) and stirred for ~30 minutes. It was then quenched with a mixture of tetrahydrofuran/water (1:1) (50 ml) and diluted with ethyl acetate (200 ml), filtered through celite, aqueous layer was separated and organic layer was washed with water (100 ml), dried over anhydrous magnesium sulfate and concentrated in vacuo to give 4 g of the title E compound, m.p. 153°–157°.

F. 2-Amino-$\beta$-(2-chlorophenyl)-$\alpha$-(hydroxymethyl)-5-(trifluoromethyl)benzenebutanoic acid, ethyl ester The solution of the title E compound (4 g, 10.8 mmol) in 100 ml of ethanol was treated with concentrated sulfuric acid (10 ml) at room temperature and heated at 65° C. for 16 hours. It was then concentrated in vacuo and purified on silica gel, eluting with 1:1 mixture of hexane and ethyl acetate to give 1.2 g of the title F compound as an oil.

G. 4-(2-Chlorophenyl)-4,5-dihydro-7-(trifluoromethyl)-1H-1-benzazepine-3-carboxylic acid, ethyl ester To a solution of the title F compound (2 g, 4.8 mmol) in dry dimethyl sulfoxide (2 ml) was added triethyl amine (1.2 g, 12.0 mmole) at room temperature and then a solution of pyridine-sulfur trioxide in dry dimethyl sulfoxide (3 ml) and allowed to stir at room temperature for 16 hours. It was then diluted with ethyl acetate (50 ml) and water (50 ml); water layer was extracted twice with ethyl acetate (100 ml) and combined ethyl acetate layers was washed twice with water (100 ml). The solution was dried over anhydrous magnesium sulfate and concentrated in vacuo. Different batches of this material were combined and purified on silica gel, eluting with a mixture of hexane/ethyl acetate (9:1) to give 0.188 g of the title compound, which was recrystallized from isopropyl ether-hexane to give 0.12 g of the title compound, m.p. 190°–192° C.

Analysis calc'd for $C_{20}H_{17}ClF_3NO_2$: C, 60.68; H, 4.33; N, 3.54; Found: C, 60.72; H, 4.30; N, 3.53.

EXAMPLES 4–29

Using the procedures outlined above and in Examples 1–3, the following additional compounds of formula I within the scope of the present invention can be made.

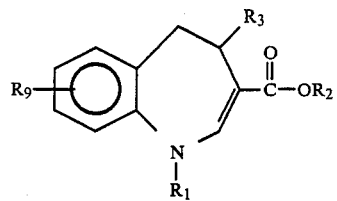
| Ex. No. | R₁ | R₉ | R₂ | R₃ |
|---|---|---|---|---|
| 4 | —H | —Cl (6-position) | —CH₃ | 2-(CF₃)phenyl |
| 5 | —H | —Br (7-position) | —C₂H₅ | 4-Cl-phenyl |
| 6 | —H | —OCH₃ (6-position) | —CH₃ | 4-CH₃-phenyl |
| 7 | —H | —CF₃ (7-position) | —CH₃ | 2,3-diCl-phenyl |
| 8 | —H | —H | —CH₃ | 2-Cl-phenyl |
| 9 | —H | —H | —CH₂—O—C₆H₅ | pentafluorophenyl |
| 10 | —H | —H | —(CH₂)₂—N(CH₃)—CH₂—C₆H₅ | 2-Cl-phenyl |
| 11 | —H | —H | —C₂H₅ | 2-Cl-phenyl |
| 12 | —H | —Cl (6-position) | —CH₂—CH—(CH₃)₂ | 2-(CF₃)phenyl |

-continued
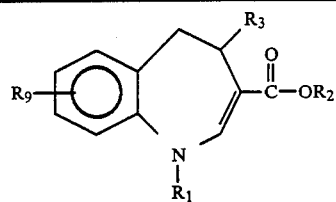
| Ex. No. | R₁ | R₉ | R₂ | R₃ |
|---|---|---|---|---|
| 13 | —H | —H | —CH₃ | 4-Cl-C₆H₄ |
| 14 | —H | —H | —(CH₂)₂—S—CH₃ | 2,6-diCl-C₆H₃ |
| 15 | —H | —H | —(CH₂)₂—S—C₆H₅ | 3-CN-C₆H₄ |
| 16 | —H | —H | —(CH₂)₂—N(CH₃)₂ | 3-Cl-C₆H₄ |
| 17 | —H | —H | —CH₂—C(O)—N(CH₃)₂ | 2,3-diCl-C₆H₃ |
| 18 | —H | —H | —CH₃ | 3-Br-C₆H₄ |
| 19 | —H | —H | —C₂H₅ | 3-Br-C₆H₄ |
| 20 | —H | —H | —CH₃ | 2-(F₂CHO)-C₆H₄ |
| 21 | —H | —H | —CH₃ | 3-Cl-C₆H₄ |
| 22 | —H | —H | —CH₃ | 2-CH₃-C₆H₄ |

-continued

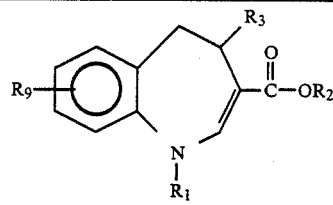

| Ex. No. | R$_1$ | R$_9$ | R$_2$ | R$_3$ |
|---|---|---|---|---|
| 23 | —(CH$_2$)$_2$—N(CH$_3$)(CH$_2$CH$_2$-(3,4-dimethoxyphenyl)) | —CF$_3$ (7-position) | —CH$_3$ | 4-methoxyphenyl |
| 24 | —(CH$_2$)$_2$—N(CH$_3$)(CH$_2$CH$_2$-phenyl) | —CF$_3$ (6-position) | —CH$_3$ | 4-methoxyphenyl |
| 25 | —(CH$_2$)$_2$—N(CH$_3$)(CH$_3$) | —Cl (6-position) | —CH$_3$ | 3-chlorophenyl |
| 26 | —(CH$_2$)$_2$—N(C$_2$H$_5$)$_2$ | —H | —CH$_3$ | 4-methylphenyl |
| 27 | —(CH$_2$)$_2$—N(4-methylpiperazinyl) | —Cl (6-position) | —CH$_3$ | 4-methoxyphenyl |
| 28 | —(CH$_2$)$_2$—N(morpholinyl) | —H | —C$_2$H$_5$ | 4-methoxyphenyl |
| 29 | —(CH$_2$)$_2$—N(piperidinyl) | —CF$_3$ (7-position) | —CH$_3$ | 4-chlorophenyl |

What is claimed is:

1. A compound of the formula

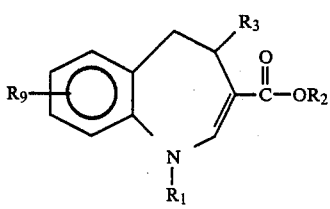

R$_1$ is hydrogen or

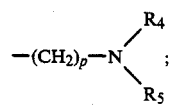

R$_2$ is hydrogen, lower alkyl, —(CH$_2$)$_m$—aryl, —(CH$_2$)$_m$—cyclo(lower)alkyl, —(CH$_2$)$_p$—OH, —(CH$_2$)$_p$—(CH$_2$)$_p$—O—lower alkyl, —(CH$_2$)$_p$—O—(CH$_2$)$_m$—aryl, —(CH$_2$)$_p$—SH, —(CH$_2$)$_p$—S—lower alkyl, —(CH$_2$)$_p$—S—(CH$_2$)$_m$—aryl,

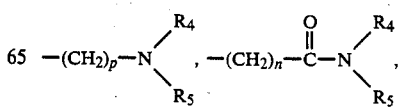

-continued

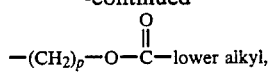

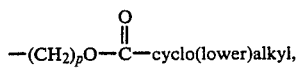

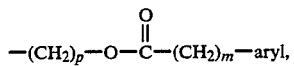

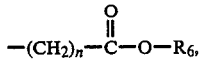

halo substituted lower alkyl, or a pharmaceutically acceptable salt forming ion;
$R_3$ is aryl;
$R_4$ and $R_5$ are independently selected from the group consisting of hydrogen, lower alkyl, —$(CH_2)_m$—aryl,

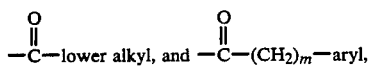

or $R_4$ and $R_5$ taken together with the N atom to which they are attached complete a heterocyclic ring of the formula

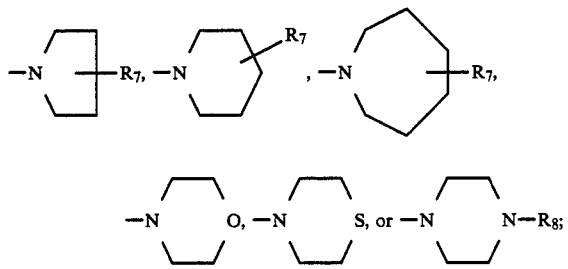

$R_6$ is hydrogen, lower alkyl, —$(CH_2)_m$—aryl, or a pharmaceutically acceptable salt forming ion;
$R_7$ is hydrogen, alkyl of 1 to 4 carbons, alkoxy of 1 to 4 carbons, alkylthio of 1 to 4 carbons, halo, $CF_3$ or hydroxy;
$R_8$ is hydrogen, alkyl of 1 to 4 carbons or $(CH_2)_m$—aryl;
$R_9$ is hydrogen, alkoxy of 1 to 4 carbons, halo or $CF_3$;
m is zero or an integer from 1 to 6;
n is an integer from 1 to 6;
p is an integer from 2 to 6;
wherein the term lower alkyl refers to straight or branched chain hydrocarbon radicals having up to eight carbons, and the terms lower alkoxy and lower alkylthio refer to such lower alkyl groups attached to an oxygen or sulfur;
the term lower alkenyl refers to straight or branched chain hydrocarbon radicals having from two to eight carbons and one double bond;
the term lower alkynyl refers to straight or branched chain hydrocarbon radicals having from two to eight carbons and one triple bond;
the term cycloalkyl refers to saturated rings of 4 to 7 carbon atoms;
the term halo refers to chloro, bromo and fluoro;
the term halo substituted lower alkyl refers to said lower alkyl groups in which one or more hydrogens have been replaced by chloro, bromo or fluoro groups;
the term aryl refers to phenyl or mono substituted phenyl, wherein said substituent is alkyl of 1 to 4 carbons, alkylthio of 1 to 4 carbons, alkoxy of 1 to 4 carbons, halo, cyano, hydroxy, amino, —N-H—alkyl wherein alkyl is of 1 to 4 carbons, —N-(alkyl)$_2$ wherein alkyl is of 1 to 4 carbons, $CF_3$, $OCHF_2$,

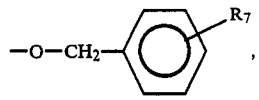

—$OCH_2$—cyclo(lower)alkyl,

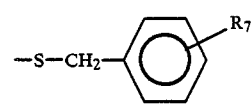

or —S—$CH_2$—cyclo(lower)alkyl, di- or tri-substituted phenyl wherein said substituents are selected from methyl, methoxy, methylthio, halo, $CF_3$, hydroxy, amino, and $OCHF_2$.

2. A compound of claim 1 wherein
$R_2$ is straight or branched chain alkyl of 1 to 5 carbons, —$(CH_2)_p$—O—alkyl wherein alkyl is straight or branched chain of 1 to 5 carbons,

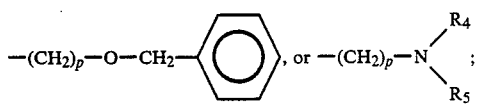

is 2, 3 or 4;
$R_4$ and $R_5$ are independently selected from hydrogen, straight or branched chain alkyl of 1 to 5 carbons, and phenylethyl or substituted phenylethyl;
wherein the substituents are selected from alkyl of 1 to 4 carbons, alkylthio of 1 to 4 carbons, alkoxy of 1 to 4 carbons, halo, cyano, hydroxy, amino, —N-H—alkyl wherein alkyl is of 1 to 4 carbons, —N-(alkyl)$_2$ wherein alkyl is of 1 to 4 carbons, $CF_3$, $OCHF_2$,

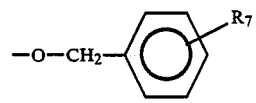

—$OCH_2$—cyclo(lower)alkyl,

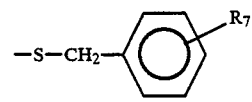

or —S—$CH_2$—cyclo(lower)alkyl in the case of mono-substituted phenylethyl; and wherein the substituents are independently selected from methyl, methoxy, methylthio, halo, $CF_3$, hydroxy, amino, and $OCHF_2$ in the case of di- or tri-substituted phenylethyl;

R3 is phenyl, 2-, 3- or 4-mono substituted phenyl wherein said substituent is alkyl of 1 to 4 carbons, alkoxy of 1 to 4 carbons, alkylthio of 1 to 4 carbons, halo, CF3, or OCHF2, disubstituted phenyl, 2,3,4-trisubstituted phenyl, 3,4,5-trisubstituted phenyl wherein said phenyl substitutents are selected from methyl, methoxy, methylthio, halo, CF3, and OCHF2, or pentafluorophenyl; and, R9 is hydrogen, Cl or CF3.

3. A compound of claim 1 wherein
R1 is hydrogen or —(CH2)2—N(CH3)2;
R2 is lower alkyl;
R3 is phenyl, 2-(trifluoromethyl)phenyl, 4-methylphenyl, 4-methoxyphenyl or 2-chlorophenyl; and,
R9 is CF3.

4. A compound of claim 1 wherein
R1 is

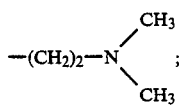

R2 is —CH3;
R3 is

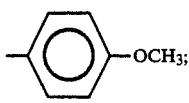

and R9 is 6-CF3.

5. A compound of claim 1 wherein
R1 is

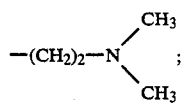

R2 is —CH3
R3 is

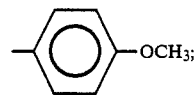

and R9 is 7-CF3.

6. A compound of claim 1 wherein
R1 is hydrogen;
R2 is —CH3;
R3 is

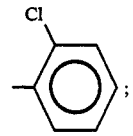

and R9 is 6-CF3.

7. A compound of claim 1 having the name 1-[2-(dimethylamino)ethyl]-4,5-dihydro-4-(4-methoxyphenyl)-7-(trifluoromethyl)-1H-1-benzazepine-3-carboxylic acid, methyl ester, fumarate (1:1) salt.

8. A compound of claim 1 having the name 1-[2-(dimethylamino)ethyl]-4,5-dihydro-4-(4-methoxyphenyl)-6-(trifluoromethyl)-1H-benzazepine-3-carboxylic acid, methyl ester oxalate (1:1) salt.

9. A compound of claim 1 having the name 4-(2-chlorophenyl)-4,5-dihydro-7-(trifluoromethyl)-1H-1-benzazepine-3-carboxylic acid, ethyl ester.

10. A composition useful in reducing blood pressure in a mammal comprising a pharmaceutically acceptable carrier and an anti-hypertensively effective amount of a compound or pharmaceutically acceptable salt thereof of the formula

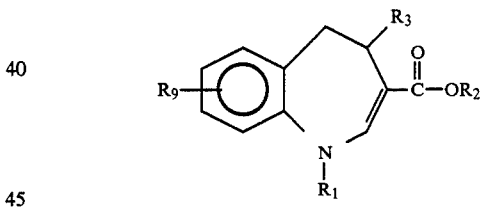

wherein R1, R2, R3 and R9 are as defined in claim 1.

11. The method of reducing blood pressure in a mammal comprising administering an effective amount of the composition of claim 10.

* * * * *

UNITED STATES PATENT AND TRADEMARK OFFICE
CERTIFICATE OF CORRECTION

PATENT NO. : 4,824,831
DATED : April 25, 1989
INVENTOR(S) : Karnail Atwal

It is certified that error appears in the above-identified patent and that said Letters Patent is hereby corrected as shown below:

Column 18, line 60, "$-(CH_2)_p-(CH_2)_p-O-\text{lower alkyl},$" should be -- $-(CH_2)_p-O-\text{lower alkyl},$ --;

Column 20, line 39, before "is 2, 3 or 4;" insert --p--;

Column 20, line 47, "CFhd 3," should be --$CF_3$,--.

Signed and Sealed this

Sixteenth Day of June, 1992

Attest:

DOUGLAS B. COMER

*Attesting Officer*      Acting Commissioner of Patents and Trademarks